United States Patent [19]
Bernaz

[11] Patent Number: 5,522,814
[45] Date of Patent: Jun. 4, 1996

[54] METHOD OF HIGH FREQUENCY DEPILATION

[76] Inventor: Gabriel Bernaz, 35 rue Marziano, Carouge 1227, Switzerland

[21] Appl. No.: 190,150

[22] PCT Filed: Sep. 1, 1992

[86] PCT No.: PCT/EP92/02010

§ 371 Date: Feb. 4, 1994

§ 102(e) Date: Feb. 4, 1994

[87] PCT Pub. No.: WO93/04636

PCT Pub. Date: Mar. 18, 1993

[30] Foreign Application Priority Data

Sep. 5, 1991 [FR] France ................................ 91 11002

[51] Int. Cl.⁶ .................................................... A61B 17/41
[52] U.S. Cl. .................................. 606/36; 606/43; 606/44
[58] Field of Search .................................. 606/36, 43, 44, 606/133, 222

[56] References Cited

U.S. PATENT DOCUMENTS

3,994,300 11/1976 Siddons ..................................... 606/36
4,498,474 2/1985 Chalmers et al. ........................ 606/36

FOREIGN PATENT DOCUMENTS

| | | |
|---|---|---|
| 0384804 | 8/1990 | European Pat. Off. . |
| 2539622 | 7/1984 | France . |
| 1717117 | 6/1971 | Germany . |
| 1187360 | 12/1987 | Italy . |
| 109802 | 7/1925 | Switzerland . |
| WO80/02640 | 12/1980 | WIPO . |

*Primary Examiner*—Angela D. Sykes
*Assistant Examiner*—Stephen D. Huang
*Attorney, Agent, or Firm*—Lahive & Cockfield

[57] ABSTRACT

The method of treating the skin (2), in particular long-lasting depilation or hair regrowth treatment, involves inducing a high-frequency electromagnetic current through the skin by means of a conductive gel (3) loaded with treating product and applied to the skin at the desired location, the electromagnetic current causing the product to penetrate the pores of the skin. The apparatus comprises a handleable member (1) making contact with the skin (2) and having a non-conductive body (10, 12) provided with a rectangular contact surface (17) having a row of individual conductive points (15) for electromagnetic emission. Said points (15) are exposed through openings in the surface, preferably recessed with respect to the latter, to make contact with loaded conductive gel (3) applied to the skin. An electric circuit (26) supplies pure emissive high-frequency current to the emission points (15), which emit it through the gel (3).

10 Claims, 3 Drawing Sheets

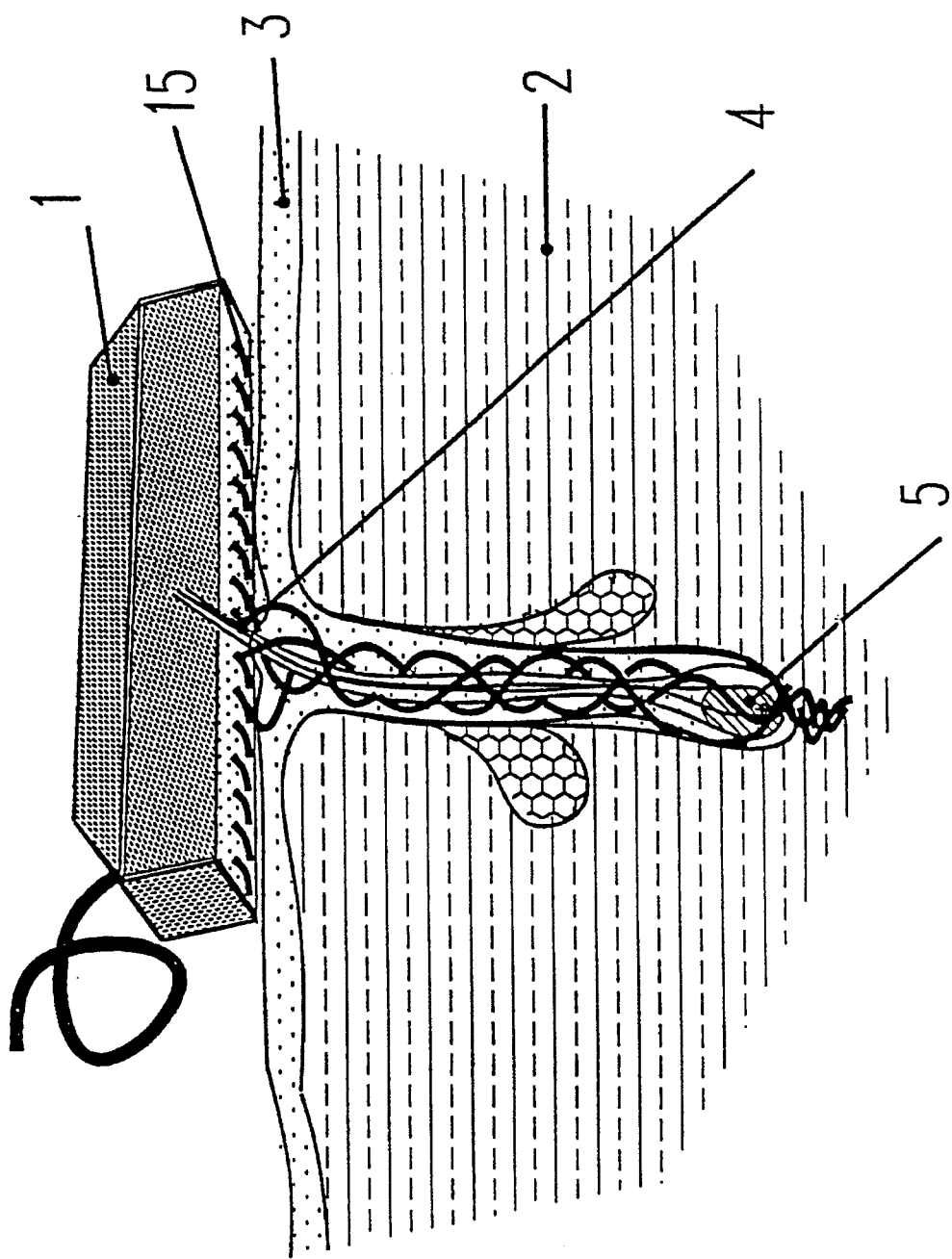

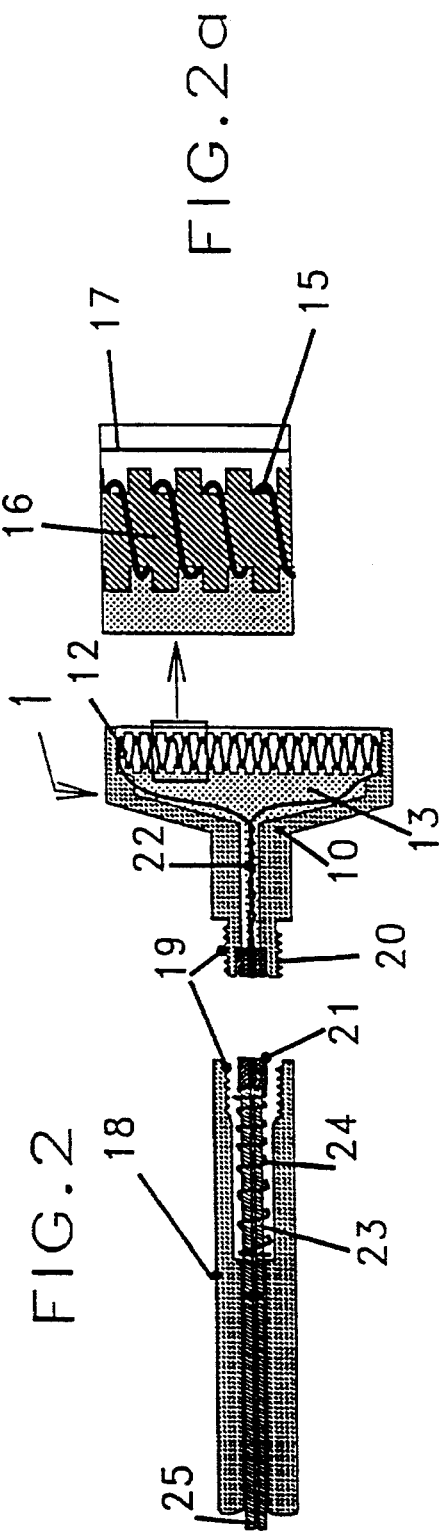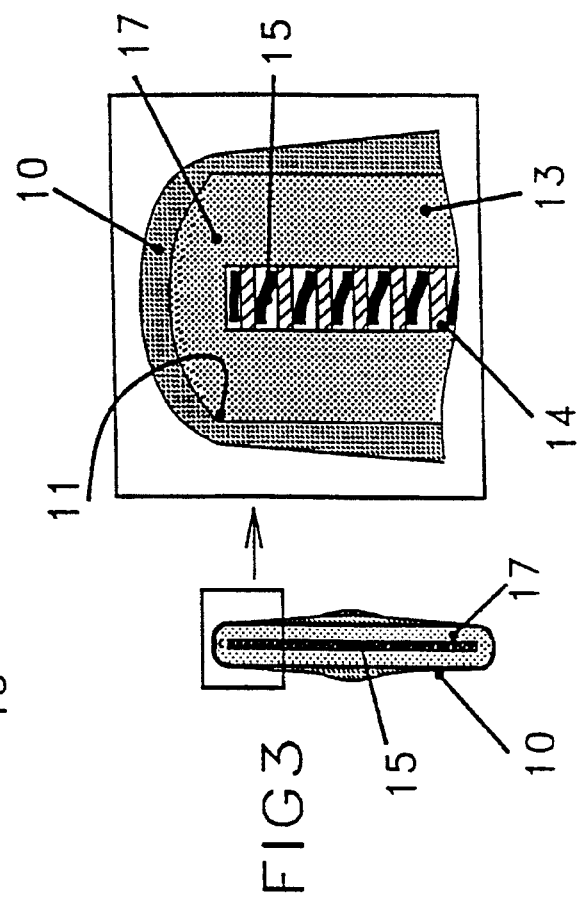

METHOD OF HIGH FREQUENCY DEPILATION

The invention relates to treatment of the skin by high-frequency electric means, particularly for so-called "permanent" or "long lasting" depilation, as well as for regrowth of hair.

There are three known high-frequency depilation methods.

One of these methods consists in devitalising the hair root by introducing a needle into the hair follicle down to adjacent the root in order to apply high-frequency energy directly thereto. This method is delicate and requires specially trained personnel. The use of a hollow needle through which, after application of a high-frequency current, passes a liquid which attacks the root, is described in DE-A-1 717 117. This apparatus is only suitable for dense pilosities.

In the second method, the lower end of the hair is grasped with tweezers connected to a high-frequency generator. The hair is progressively extracted after several tens of seconds. For example, WO80/02640 describes the use of a conductive solution that wets the hair in the follicle, and the application of a HF current by means of tweezers. The current is applied for up to 20 seconds. This method is not very effective.

In the third method, high-frequency current is applied to the skin by means of a flat disk. This method also proved to be ineffective because it does not allow a punctual application. Moreover, the use of an oxidising solution with application of a low voltage of 4 to 5 volts by means of flat electrodes, according to CH-109802, is also an ineffective method.

For hair regrowth, the use of insulated probes operating at high frequencies has already been proposed for the purpose of causing penetration of a hair regrowth product. The results have not been conclusive.

FR-A-2 539 622 describes a composition for treating the scalp by electrophoresis, consisting of a photosensitive aminovinylic solution usually dissolved in a saline alcoholic solution, possibly with the addition of one or more nutrients. The electrophoresis takes place by applying a two-phase low-frequency wave, one phase having a frequency of the order of 50 to 300 Hz on a square wave having a frequency of the order of 0.5 to 2 Hz.

Moreover, EP-A-0 384 804 describes a conductive facemask comprising a settable composition composed of a gel which is stable when out of contact with the air, but which polymerizes in contact with the air. When this product is applied to the skin, it becomes consistent and for a period of time, a pulsed voltage at low-frequency comprised between 40 and 110 Hz can be caused to flow to produce a therapeutic or an esthetic effect.

These low-frequency treatments do not form part of the invention which concerns a method of cosmetic treatment by applying to the skin a treating product able to act on the hair roots, and by applying a high-frequency electromagnetic current.

The invention is based on the observation that by mixing a conductive gel of the usual type used for the application of ultrasound probes to the skin, with a treating product, for example a lotion producing atrophy of the hair roots, it is possible by transcutanous induction at high frequency to cause the treating product to penetrate into the pores and hence carry out a treatment.

This thus leads to a new, notably cosmetic, method of treating the skin, for example to achieve a long lasting depilation, and which moreover allows a punctual and effective application down to the follicles without a delicate manual intervention. Of course, the same technique may also be suitable for introducing other cosmetic products into the skin, for example for hair regrowth, or against wrinkles, as well as pharmaceutical products, for example for treating acne, seborrhea, wounds, or pains.

The invention, as defined in the claims, concerns a method of and an apparatus for long lasting depilation and other treatments of the skin, which are easy to use and effective. The invention concerns also the use of the apparatus for depilation or for hair regrowth, the cosmetic use of the gel/product mixture, as well as the mixture of the gel and of the product used with the apparatus or when carrying out the method, and a novel high-frequency-generating electric circuit.

The apparatus according to the invention comprises a handleable member for contacting the skin, having a non-conductive body provided with a contact surface adapted to be applied to the skin. This surface comprises a plurality of distinct conductive electromagnetic emission points for example formed by exposed parts of turns of a solenoid embedded in the body of the handleable member. These points are exposed through openings in this surface, and are preferably recessed with respect to the latter, so that during use of the apparatus, these points may contact loaded conductive gel applied to the skin. These discrete electromagnetic emission points emit high-frequency current, advantageously a pure emissive current supplied by an oscillatory high-frequency power circuit.

The handleable member thus forms a focalised probe whose high-frequency energy produces a punctual action through the loaded gel. By arranging the discrete emission points in a suitable manner on the contact surface, a simultaneous action is obtained on all of the follicles of an extensive area of the skin. For example, the discrete emission points are aligned in one or several rows along an oblong contact surface whose dimensions are adapted to the part of the body to be treated. Preferably, several interchangeable handleable members are provided having contact surfaces of different shapes and/or of different sizes, and possibly also an interchangeable needle fitment, thus enabling treatments suitable for all types of pilosity.

The high-frequency electric generator circuit advantageously comprises a high-frequency oscillatory power circuit comprising a transistor connected as a power oscillator in combination with double-square-winding self-inductance coils, and an electrode by means of which the impedance of a treated person's body may be added to that of the self-inductance coils to increase the frequency of the emissive current during use.

BRIEF DESCRIPTION OF DRAWINGS

Further features of the invention will be apparent from the following description, given by way of example, with reference to the drawings in which:

FIG. 1 is a diagram illustrating a depilatory treatment according to the invention, FIG. 2 is a schematic axial cross-section of a contact member of an apparatus according to the invention, whereof FIG. 2a shows a detail on an enlarged scale, FIG. 3 is a front view of the contact member of FIG. 2, FIG. 3a showing a detail on an enlarged scale.

DETAILED DESCRIPTION

Figure 4:
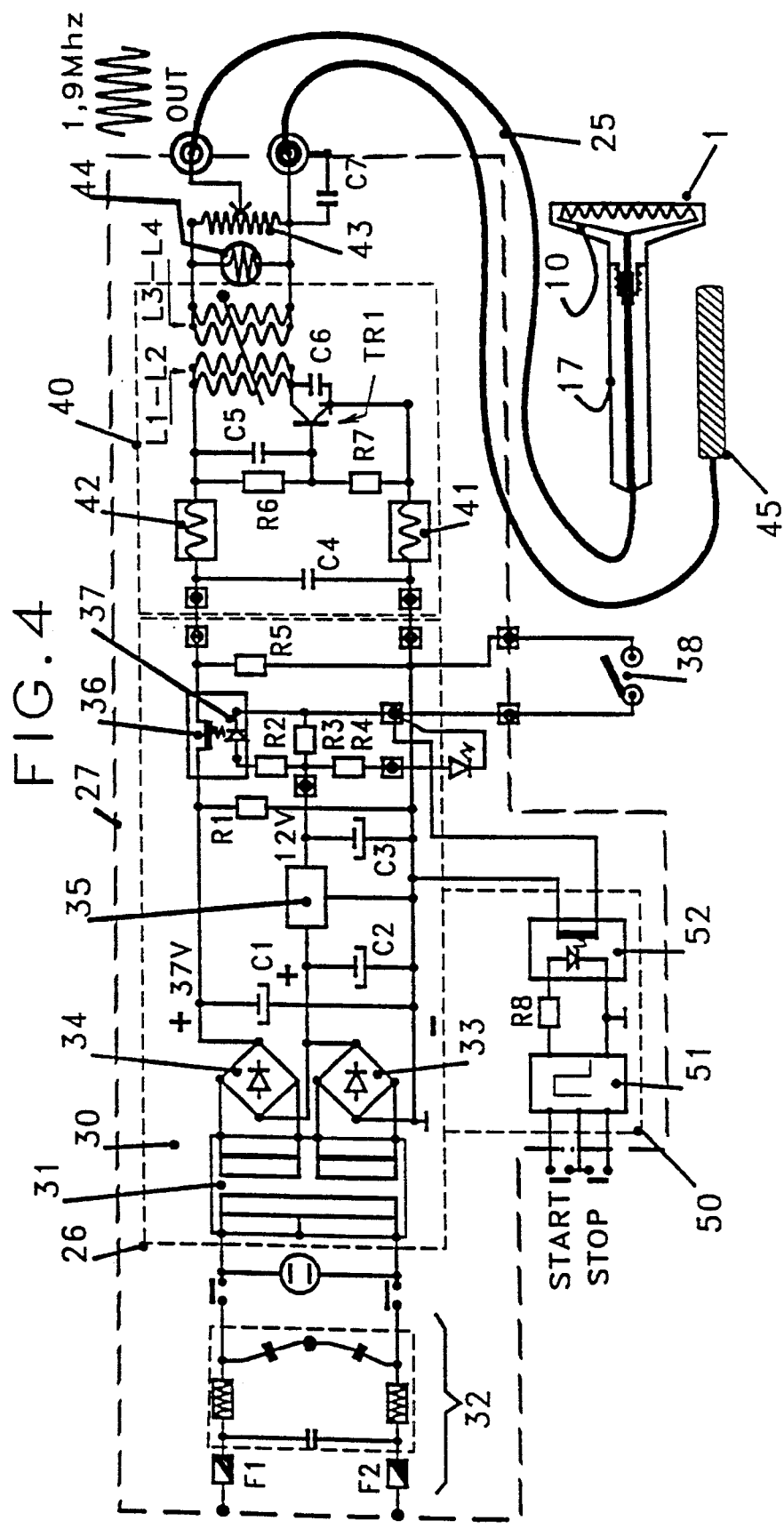
FIG. 4 is a diagram of the electric circuit of the apparatus according to the invention.

FIG. 1 schematically shows a probe 1 applied onto skin 2 covered with a conductive and wetting gel 3 containing a bioactive product. By applying high-frequency energy emitted by emission points 15 of probe 1, a conductive solution derived from the loaded gel 3 and containing the bioactive product penetrates into the pore of a hair down to the root 5.

The loaded gel 3 is composed of a conductive gel of a type used usually for coupling ulstrasound probes with the skin, mixed with a bioactive product. The gel has a neutral pH and is for example based on a polymer of 5-bromo-5-nitro-1,3-dioxane-2-carboxyvinylic ester. The composition of the bioactive product depends on the desired action. For depilation, one may choose a product providing a progressive atrophy of the hair root, for example a post-depilatory lotion of the type usually used immediately after wax-depilation, as well as during the subsequent days. Such lotions comprise plant extracts, essential oils, demineralised water and possibly other components, for example polyoxethylenes. These products, known sometimes as "hair regrowth moderators" are non-toxic and generally risk-free when used.

For treating baldness, the gel may be mixed with, for example, minoxydil, or another product promoting hair regrowth. A mixture of 50:50 volume % of gel and minoxydil has given satisfactory results.

In order not to diminish the conductive properties of the gel, the quantity of active or treating product will in general not exceed 50 weight % of the gel, usually less than 25% (% by weight=% by volume). Alcohol, sodium chloride and/or other substances may be added to improve the conductivity of the product and/or as conserving agents.

Tests have shown that applying high-frequency energy to the bioactive product alone or to the gel alone does not produce any special effect, whereas with the mixture a good penetration of the bioactive product carried by the conductive solution derived from the gel is obtained. It appears that the conduction of electromagnetic and electric energy follows the path of least resistance through the gel and conductive lotion mixture applied to the surface of the skin, and then, around the hair root, only through the conductive lotion which penetrates into the pore. The gel allows a progressive release of the active lotion and penetration thereof, under the conjugated action of the electromagnetic and electric fields. This synergistic effect could not have been predicted.

The high-frequency current has an excellent coefficient of absorption in the skin, because the system behaves like a radio emitter-receiver. For this purpose, a pure high-frequency emissive current, exempt of harmonics, is preferably used.

The energy of the high-frequency current is focalised onto the skin by the emission points 15 situated on the part of probe 1 which is in contact with the loaded gel 3. This energy follows the conductive solution and carries with it the active product into the follicle, causing a progressive heating accompanied by dilatation of the hair follicle, which favors the penetration of the active product and increases the effectiveness of the latter's action on the hair root. This produces intraroot ionothermolysis of the hair, by effective penetration of the conductive and bioactive solution.

It thus suffices to slowly move the probe 1 to produce softening of the hair follicle after a few minutes, and, in the case of a depilatory treatment, atrophy of the hair root, thus assisting its extraction by the classic means of cold wax, for example. Several sessions are necessary to produce permanent atrophy of the hair.

For hair regrowth, the same method of application serves to cause penetration of the treating product into the hair root and increases its effectiveness. This method applies not only for the regrowth of the scalp's natural hair, but also to transplanted hair to increase the effectiveness of the transplant.

The probe 1, which constitutes a handleable member for contacting the skin 2, is shown in greater detail in FIGS. 2 and 3. It comprises a hollow body 10 of plastics material, having at its front end an oblong mouth 11 and enclosing a solenoid 12 embedded in a mass 13 of resin, except facing the mouth 11 where the mass 13 has an opening 14 where a portion 15 of each turn of the solenoid 12 is exposed. These portions 15 constitute the conductive focalised emission points that contact the loaded gel 3.

The solenoid 12 is for example made of non-magnetic cobalt-nickel wire having a cross-section of 0.35 mm$^2$ wound in the thread of a threaded rod 16 of plastics material, for example of 7 mm diameter. The thread for example has a pitch of 1 mm and its bottom is situated about 3 mm below the exposed surface 17 of the mass 13 so that the points 15 do not enter into direct electrical contact with the skin when this surface is applied thereupon.

The points 15 accessible through opening 14 thus form windows for electric and electromagnetic conduction towards the loaded gel 3. These points 15 are preferably aligned in one or more rows along the oblong contact surface 17. Other arrangements are possible, but the oblong form with a single row of points, as illustrated in FIGS. 3 and 3a, has the advantage of avoiding possible interference.

The probe 1 is removably secured on a handle 18 by means of threads 19. These threads 19 bring two sockets 20 and 21 into contact, the socket 20, arranged in body 10, being connected by wires 22 to the ends of solenoid 12, whereas the socket 21, slidably fitted on the end of a rod 23 inside handle 18, is connected firstly by a spring 24 surrounding the rod 23, then by a wire 25, to circuit 26 shown in FIG. 4.

To enable effective treatments on different parts of the body, and effective treatments of different types of pilosity, several probes 1 of different shapes and/or dimensions may be selectively and removably fitted on handle 18. For example, a first probe 15 mm long can be provided for the mustache, another 25 mm long for the face and the front of the body, and a third 45 mm long for the back and legs. For treating large surfaces, a rectangular probe provided with several rows of emission points well spaced from one another, advantageously by sector-by-sector sweeping action of the electromagnetic and electric current, may be provided. It is also possible to provide a needle fitment interchangeable with the probes 1 enabling use, in specific cases, of the classic high-frequency depilation method using a needle.

This circuit 27 is contained in a housing and comprises supply circuit 26 including a stabilised double supply 30 followed by an oscillatory circuit 40 delivering at its output a current of low amplitude and very high frequency.

In conventional manner, there is an input transformer 31 connected to the mains via a suppressor circuit 32. A first secondary winding of transformer 31 is connected by a diode bridge 33 inducing a DC voltage of 12 V stabilised by capacitors C2, C3 and a first integrated circuit 35. A second winding of transformer 31 is connected to a second diode bridge 34 adding a second voltage of the order of 25 V to the previously-mentioned 12 V to produce a total DC voltage of 37 V. This second voltage is adjusted by capacitor C1 and by a second integrated circuit 36 which is switched on or off by a start-up and time delay circuit 50 via an emitting diode 37.

This circuit 50 comprises an integrated circuit 51 producing time pulses connected to emitting diode 37 by an optoelectronic connection 52.

The oscillatory circuit 40 comprises a transistor TR1, connected to form a common emitter with double-square-winding self-inductance coils L1–L2 connected between the collector of transistor TR1 and the positive supply terminal, the base of transistor TR1 being connected, firstly, to the middle of a voltage-adjusting resistance bridge R6, R7 and, secondly, to the positive supply terminal via a capacitor C5 of 1.2 nF. A second capacitor C6 of 330 picofarad connects the collector and emitter of transistor TR1.

Due to the interaction of capacitor C5 on the base and the impedance of the self-inductive coils L1–L2 on the collector, transistor TR1 operates as an oscillator. Inductances 41 and 42 prevent the oscillations of transistor TR1 from passing upstream into the supply circuit 30.

The oscillations generated in the inductance of coils L1–L2 are retransmitted with a doubling of the frequency in the secondary self-inductance coils L3–L4 (according to the same principle as a transformer) whose circuit is closed by a potentiometer 43, with a 50 V voltage limiter or "shunt" 44 connected in parallel, by means of which a fraction of the voltage may be taken off still at the same amplified frequency. The output of potentiometer 43 is connected to a base electrode 45 and to the high-frequency probe 1. The potentiometer 43 can be replaced by an integrated circuit and a potentiometer (voltage regulator) connected in the supply circuit 30.

The high-frequency current is thus produced by the transistor TR1 connected as a self-oscillatory power oscillator.

The self-inductance coil L1–L2 is provided on a printed circuit with a pair of parallel square-wound windings, superposed with a spacing of 1.6 mm. This self-inductance coil is situated at a distance of 4 to 6 mm from the second self-inductance coil L3–L4, also with parallel double-square-wound windings, superposed with a 1.6 mm spacing. The self-inductance L3–L4 is thus tuned with the self-inductance L1–L2.

This design of the self-inductance enables the transistor TR1 to oscillate as a frequency doubler producing a dynamic reaction on the oscillator leading to a proportional increase of the frequency from 1.9 MHz to 3 to 4 MHz, by means of electrode 45 connected to the self-inductance coil L3–L4, which results in the impedance of the treated person's body being added to that of the windings of the self-inductance coil L3–L4.

Compared to conventional quartz-driven circuits used in this field, and which operate at fixed frequency, this circuit supplies a pure emissive high-frequency current, thus exempt of harmonics, which ensures an effective transmission by the points 15 of probe 1. However, this circuit can also advantageously be used for other uses, notably for high-frequency depilation using a needle. Hence, its field of application is not limited to the method employing a loaded conductive gel.

Operation of oscillator circuit 40 is controlled either by actuating a pedal 38, or by manual control of the self-stopping time delay circuit 50 and switching of the optoelectronic circuit 52. In the first case, the probe 1 emits as long as pressure is applied to pedal 38. In the second case, which for example is used when the probe 1 is held stationary on a given location of the skin, the probe emits during a pre-adjusted time. Optionally, a timing device can be provided for setting the working time.

The synergistic action obtained with the mixture of gel and treating product according to the invention is clearly evident from the examples below.

EXAMPLE I (COMPARATIVE)

ELECTROGEL™ conductive gel produced by Messrs. Diaplix and used for echography and electrocardiography was applied on a pilous region of the skin measuring approximately 5 cm×5 cm. By means of the apparatus according to the invention as described and as illustrated in the drawings, an electromagnetic current at a frequency of 2 MHz was applied for a period of 10 to 20 minutes. No effect was observed. The gel did not penetrate into the pores nor did it produce any modification in the resistance of the hair to extraction.

EXAMPLE II (COMPARATIVE)

BANNIPIL™ post-depilatory lotion was applied on a pilous region of the skin measuring approximately 5 cm×5 cm and submitted to the same treatment by the described apparatus according to the invention. This post-depilatory product is based on plant extracts (birch, horsetail and hamamelis) and essential oils (a distillation product of lemon, verbena and lavender) and further comprises propylene glycol, fatty acids, polyoxyethylenes and demineralised water. At the end of the treatment, no effect was observed. The product had not penetrated into the pores. The hair root had not been reached. The resistance of the hair to extraction was unchanged.

EXAMPLE III

A mixture of 89 vol % of ELECTROGEL™ gel, 9 vol % of BANNIPIL™ post-depilatory lotion and 2 vol % of 90° surgical spirit (rubbing alcohol) containing NaCl was prepared. This mixture was applied to a pilous region of the skin measuring 5 cm×5 cm. By means of the described apparatus according to the invention, an electromagnetic current at a frequency of 2 MHz was applied for a period of 10 to 20 minutes as previously. A penetration of the lotion into the pores was observed. This penetration enables resistance-free extraction of the hairs. An examination of the root by microscope (magnification times 150) shows that the structure of the hair root is smooth, softened and has shrunk, which indicates that the lotion has penetrated into the pore and has produced an effect. This effect is to remove the keratinous membrane of the hair, which facilitates extraction thereof.

EXAMPLE IV

A mixture of 47.5 vol % of ELECTROGEL™ gel and 47.4 vol % of minoxydil and 5 vol % 90° surgical spirit containing NaCl was prepared. This mixture was applied to a pilous region of the skin, whose initial pilosity was 5 to 10% of the normal pilosity of the scalp, measuring approximately 5 cm×10 cm. By means of the described apparatus according to the invention, en electromagnetic current having a frequency of 2 MHz was applied for a duration of 15 to 20 minutes. This treatment was carried out twice a week for three weeks, then after a rest period of fifteen days, the treatment was continued with one application per week for eight weeks. At the end of the treatment, the pilosity was 15–20% of the normal pilosity of the scalp, and the quality of the hair was improved as regards the mechanical resistance and the hardness of the hair. The color of the hair was also darker. This treatment thus had a nutritive effect on the hair and improved the vitality of the hair. This result represents a substantial improvement compared to what may be obtained solely by the application to the scalp of minoxydil or another hair growth product, with or without the application of a HF current.

I claim:

1. In a method of cosmetic treatment comprising applying to an area of a person's skin which has follicles containing hair roots a treating product able to act on the hair roots and applying a high-frequency electromagnetic current, the improvement comprising the steps of:

applying to said area of the person's skin (2) a layer formed of a mixture of this treating product and of a non polymerisable conductive gel (3) of a type used usually for coupling ultrasound probes with the skin, contacting the applied layer of gel/product mixture with an electrical non-conductive body having a non-conductive contact surface with a plurality of discrete electromagnetic emission points, said applied layer forming a conductive interface layer between said emission points and said area of the person's skin, emitting the high-frequency electromagnetic current from the plurality of discrete electromagnetic emission points into the conductive interface layer of gel/product mixture applied onto said area of the person's skin to produce a high frequency electromagnetic field in the conductive interface layer which progressively releases from the gel/product mixture a conductive solution containing the treating product, and continuing to emit said high frequency emission into the conductive interface layer for at least a few minutes to cause the product, within said conductive solution derived from the mixture, to penetrate into the follicles of the skin down to the hair roots over said area of the person's skin.

2. A method according to claim 1 for long lasting depilation of an area of skin of a person's body which has hairs growing from follicles containing hair roots, comprising applying to the skin (2) a conductive interface layer made of a mixture of said conductive gel (3) and of a product producing atrophy of the hair roots, causing this product to penetrate into the follicles of the skin down to the hair roots by the high-frequency emission in the conductive interface layer, and removing the hairs by suitable means acting over said area of the person's skin.

3. The method according to claim 2 wherein the hairs are removed by means of wax.

4. The method according to claim 2, for long lasting depilation wherein said method comprises the step of preparing said mixture of the conductive gel and said bioactive treatment product and wherein said product comprises a lotion able to atrophy the hair roots, comprising plant extracts and essential oils.

5. A method according to claim 1 for cosmetic treatment of baldness, characterised in that a mixture of said conductive gel (3) and of a hair regenerating product is applied to the scalp, and this product is caused by the high-frequency emission to penetrate into the follicle of the skin down to the hair roots.

6. A method according to claim 1, comprising the step of emitting a pure high frequency emissive current into the conductive interface layer (3) by one or several rows of discrete electromagnetic emission points (15).

7. The method according to claim 1 wherein said high frequency emission into the conductive interface layer is continued for about 10 to about 20 minutes to cause the product, within said conductive solution derived from the mixture, to penetrate into the follicles down to the hair roots over said area of the person's skin.

8. A method for long lasting cosmetic depilation of an area of a person's skin which has hairs growing from follicles containing hair roots using an apparatus for transcutaneous induction of a high-frequency electromagnetic current, said apparatus comprising a handleable member (1) for contacting the skin (2), having a non-conductive body (10,13) provided with a non-conductive contact surface (17) adapted to be applied to the skin, this non-conductive surface (17) having a plurality of discrete conductive electromagnetic emission points (15), said method comprising the steps of applying said contact surface (17) to said area of the skin to be treated (2), covered with a conductive interface layer formed of a non-polymerisable conductive gel (3) of a type used usually for coupling ultrasound probes with the skin, loaded with a product able to atrophy the hair roots, emitting a high-frequency emissive current by said points into the applied conductive interface layer to produce a high frequency electromagnetic field in the conductive interface layer which progressively releases from the gel/product mixture a conductive solution containing the treating product, causing the product within said conductive solution derived from the mixture to penetrate into the follicles of the skin down to the hair roots over said area of the person's skin by continuing emission of said high frequency emissive current emitted by said points (15), into the conductive interface layer for at least a few minutes, and removing the hair afterwards by suitable means acting over said area of the person's skin.

9. The method according to claim 8, wherein the hairs are removed by means of wax.

10. The method according to claim 8 wherein said high frequency emission into the conductive interface layer is continued for about 10 to about 20 minutes to cause the product within said conductive solution derived from the mixture, to penetrate into the follicles down to the hair roots over said area of the person's skin.

* * * * *